United States Patent [19]

Chester

[11] Patent Number: 4,479,800

[45] Date of Patent: Oct. 30, 1984

[54] INJECTING NEEDLE WITH INCLINOMETER

[76] Inventor: Martin H. Chester, 25310 Tierra Grande Dr., Carmel, Calif. 93923

[21] Appl. No.: 489,975

[22] Filed: Apr. 29, 1983

[51] Int. Cl.³ ............................................... A61M 5/32
[52] U.S. Cl. ....................................... 604/187; 33/365
[58] Field of Search .................. 604/187, 218; 33/365

[56] References Cited

U.S. PATENT DOCUMENTS

| | | | |
|---|---|---|---|
| 2,402,245 | 6/1946 | Freeland | 604/187 X |
| 2,411,165 | 11/1946 | McBride | 33/365 |
| 2,452,697 | 11/1948 | Stabler | 604/187 X |
| 4,031,890 | 6/1977 | Homan | 604/187 |

*Primary Examiner*—John D. Yasko
*Attorney, Agent, or Firm*—Sughrue, Mion, Zinn, Macpeak & Seas

[57] ABSTRACT

A syringe and injection needle assembly with a gravity-responsive inclinometer for indicating the angle of inclination of the needle relative to a patient's skin. A plastic coupling tube for insertion between the syringe and needle of a conventional syringe and injection needle assembly and having means for mounting the inclinometer. The coupling tube may have an auxiliary inlet for receiving a second syringe, in which case a three-way valve is incorporated in the coupling tube for selectively providing fluid flow communication between the two syringes and the injection needle. The coupling tube may also be used without the inclinometer for the purpose of providing means for coupling a second syringe to the injection needle.

9 Claims, 8 Drawing Figures

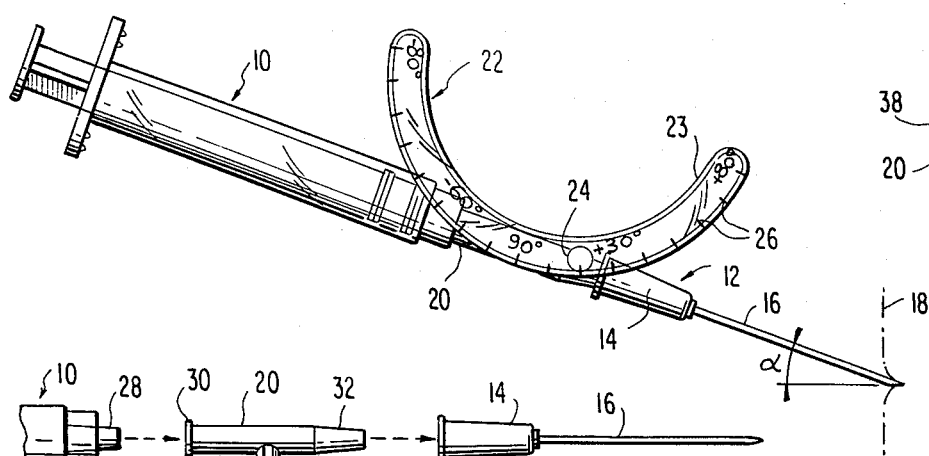
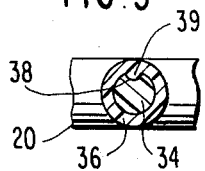
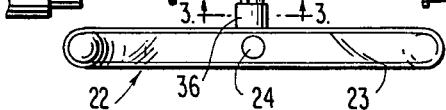
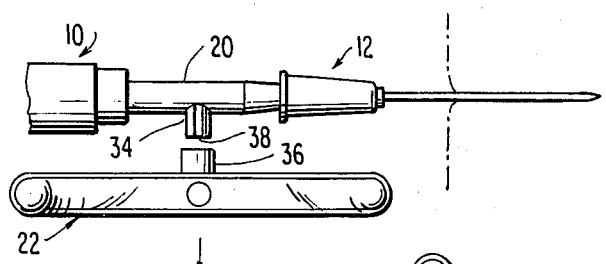
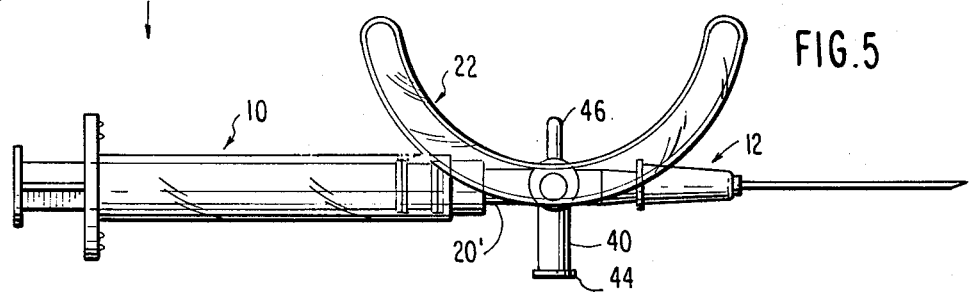
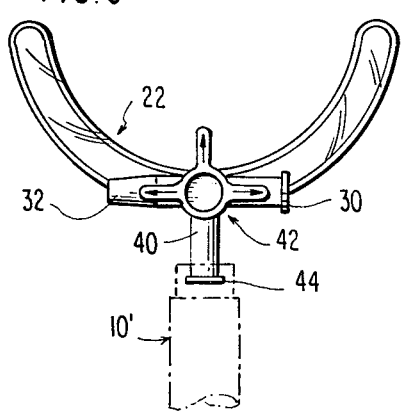
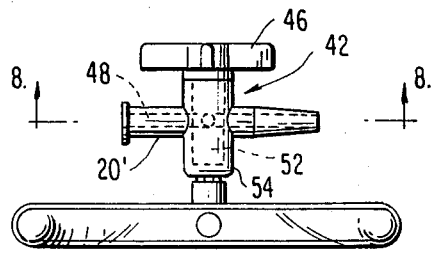
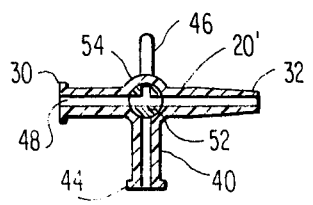

INJECTING NEEDLE WITH INCLINOMETER

BACKGROUND OF THE INVENTION

1. Field of the Invention

My invention relates to injecting needles for injecting fluids into the human body and, more particularly, to such an injecting needle carrying an inclinometer which indicates to the physican the angle at which the needle is inserted into the skin.

2. Description of the Prior Art

The anesthesiologist is frequently required to inject deep nerves with a local anesthetic solution or a neurolytic solution for nerve blockade. A successful nerve block depends on correct placement of the injecting needle. In particular, many blocks of nerves near skeletal structures require precise insertion of the injecting needle; that is, the needle must be inserted at a specific angle to the skin so that the needle is directed toward the required nerve.

For example, in caudal epidural anesthesia the needle is inserted into the caudal canal at an angle of 30 to 45 degrees in the female and 10 to 20 degrees in the male. In intercostal nerve blocks the needle forms an 80 degree angle with the skin. In a celiac plexus block the needle is introduced at an angle of 45 degrees and increased to 60 degrees when the needle contacts the lumbar vertebra. In a paravertebral lumbar sympathetic ganglion block the needle is inserted at an angle of 45 degrees to the skin, and, when the transverse process is contacted, the angle is changed to 85 degrees.

U.S. Pat. no. 4,031,890 discloses an I.V. injector which is provided with a safety disc so that the angle of entry of the cannula with respect to the skin surface always will be at least 45 degrees.

U.S. Pat No. 2,411,165 discloses a gravity-responsive clinometer in which the angle of inclination is determined by the position of a ball confined within a curved slot provided with a scale graduated in degrees.

SUMMARY OF THE INVENTION

Therefore, the primary object of my invention is to provide an injecting needle with an inclinometer which will indicate to the doctor the angle of inclination of the needle relative to the patient's skin.

Another object of my invention is to provide such an inclinometer in the form of an inexpensive gravity-responsive inclinometer in the form of a transparent arcuate tube containing a ball whose position in the tube indicates the angle of inclination to the physician.

A further object of my invention is to provide such a inclinometer in the form of a coupling which can be inserted between the syringe and needle of a conventional injecting needle and syringe assembly.

An additional object is to provide such an inclinometer which can be detached from the coupling once the needle has been inserted at the desired angle.

Still another object of my invention is to provide the coupling with a manually controllable valve and with means for attaching a second syringe thereto after the contents of the first syringe have been injected, the valve functioning selectively to provide a second flow path for directing the contents of the second syringe into the injecting needle.

My invention may be broadly summarized as an injecting needle and syringe assembly including an inclinometer for indicating to the physician the angle of inclination of the needle relative to the patient's skin.

Other features of my invention include: a coupling which can be inserted between the syringe and needle of a conventional injecting needle and syringe assembly, the coupling serving as the means for detachably mounting the inclinometer on the assembly; and providing the coupling with means for attaching thereto an additional syringe whose contents can be directed into the injecting needle by the operation of a valve formed in the coupling.

BRIEF DESCRIPTION OF THE DRAWING

FIG. 1 is a side elevational view illustrating one embodiment of my invention; i.e. a conventional syringe and injecting needle assembly modified to incorporate a gravity-responsive inclinometer for indicating the inclination angle $\alpha$ relative to the patient's skin.

FIG. 2 is a top view of FIG. 1 and is partially exploded to show the coupling on which the inclinometer is mounted.

FIG. 3 is a sectional view taken along line 3—3 of FIG. 2.

FIG. 4 is a partial top view illustrating the detachable nature of the inclinometer.

FIG. 5 is a side elevational view showing a second embodiment of the invention wherein the coupling of the preceding figures has been modified to include means for attaching thereto a second syringe.

FIG. 6 is an opposite side elevational view of FIG. 5.

FIG. 7 is a top view of FIGS. 5 and 6; and

FIG. 8 is a cross-sectional view taken along line 8—8 of FIG. 7.

DETAILED DESCRIPTION OF THE PREFERRED EMBODIMENTS

FIG. 1 illustrates the basic elements of the preferred embodiment of the broadest feature of my invention. A conventional syringe and injecting needle assembly includes a disposable injection syringe assembly 10 and an injection needle assembly 12 which are normally directly detachably coupled together. The needle assembly 12 includes a plastic bushing 14 to which the injection needle 16 is fixed. In this illustration, the needle 16 forms an angle $(90° - \alpha)$ relative to the plane 18 of the patient's skin, where $\alpha$ is the angular displacement of the needle from the perpendicular to plane 18. A plastic coupling tube 21 is inserted between the syringe assembly 10 and the bushing 14, thereby interconnecting the syringe assembly 10 and the needle assembly 12 and permitting the fluid in the syringe assembly to pass through the coupling tube 20 and into the needle assembly 12.

An inclinometer 22 is secured to the coupling 12 and provides to the physician an indication of the angle $\alpha$. Inclinometer 12 consists of an arcuate transparent hollow tube 22 in which is disposed a steel ball 24 which rolls freely along the tube's lower surface portion which functions as a track for the ball. Along the curved length of the tube are graduations 26 calibrated in + or − degrees of the inclination angle $\alpha$ from the perpendicular. Since the inclinometer 22 is fixed to the coupling tube 20, the inclinometer tube 22 will move in a vertical plane as the needle 16 is rotated through the angle $\alpha$. Since the ball 24 is loosely disposed within the tube and freely rollable therein, the tube 22 will move relative to the ball which gravity will cause always to seek the lowest point within the tube, assuming the plane 18 is vertical. Thus, the position of ball 24 within the tube 22 will be a measure of the angle α which, for the illustrated example, is approximately ±20 degrees, indicating that the needle is inclined upwardly or in the clockwise direction 20 degrees from the normal or perpendicular to the skin plane 18. If the needle were inclined at the same angle α from the perpendicular, but in the downward or counterclockwise direction, the ball would be opposite the −20 degree graduation. Of course, if the needle were horizontal, i.e. perpendicular to the vertical skin plane 18, then the ball would be opposite the 90 degree graduation. The graduations may be marked with any desired scale, such as degrees from the plane of the skin. The graduations can be calibrated according to any particular curve of the tube 22 so that the ball 24 will always indicate a measure of the angle of inclination.

FIG. 2 and 3 show in more detail the construction of the coupling tube 20 and the manner in which the inclinometer 22 is mounted thereon. The larger diameter left end 30 of tube 20 slides over the tapered male connecting tube 28, which is an integral part of the plastic syringe assembly 10, such that a friction fit is formed so that tube 28 and end 30 form a tight, leak-proof friction fit. The right hand or male end 32 of the coupling tube 20 is tapered and forms a tight friction fit with the interior of the needle bushing 14. Molded integrally with the tube coupling 20 is a projecting post 34 which forms a friction fit with a bushing 36 molded integrally with the plastic tube 23. Post 34 has an axial recess 38 along its surface for receiving a matching key or radially inwardly projection 39 of bushing 36, thereby preventing rotation of the inclinometer bushing 36 relative to the mounting post 34, but permitting the physician to remove the inclinometer from the post by applying outward force to overcome the friction fit of the two members. Such a construction permits the physician to remove the inclinometer, if desired, after the needle has been inserted in the patient's skin at the desired angle.

FIG. 4 illustrates the detachable nature of the inclinometer.

FIGS. 5–8 illustrate another embodiment of my invention and the same reference numerals are used to indicate corresponding parts of the two embodiments. In this second embodiment, a modified coupling tube 20′ is inserted between the syringe assembly 10 and the needle assembly 12 in the same manner as already described. However, also molded integrally with the coupling tube 20′ are an outwardly projecting bushing 40 and a 3-way stopcock or valve assembly 42. The open end 44 of the bushing 40 has the same internal diameter as the open end 30 of the coupling tube 20 (FIG. 2) and, therefore, can receive the tapered male connecting tube 28 of a second conventional syringe assembly 10′The bore of the bushing 40 is in selective fluid communication with the bore through the coupling 20′ via the 3-way stopcock 42. This feature allows a physician to attach a second full syringe 10′ to the needle assembly after the contents of the first syringe assembly 10 have been injected, and without having to remove the first syringe 10.

The molded valve assembly 42 has an operating knob 46 containing three projections carrying arrows indicating which flow path has been selected by the rotational position of the valve. For example, in the position illustrated in FIG. 6 and 8, the flow path to the second syringe assembly 10′ is blocked, while the flow path through the length of the coupling tube 20′ is open so that the contents of the first syringe 10, coupled to the end 30 of the coupling tube 20′, will flow through the bore 48, through the valve 42 into the needle assembly 12 attached to the tapered end 32 of the coupling tube 20′. When it is desired to inject the contents of the second syringe 10′ into the patient, then the valve 42 is rotated 90 degrees counterclockwise from the position shown in FIG. 6 (clockwise in FIG. 8), thereby placing the internal bore 50 of the bushing 40 into fluid communication with the right hand portion of the bore 48 in the coupling tube 20′. The valve handle 46 is molded integrally with a valve core 52 which has three ports as clearly shown in FIG. 8. The valve core is molded within the valve casing 54, which is molded integrally with the coupling tube 20′, in such a way that the valve core may be rotated relative to the casing but cannot be moved axially relative thereto. In this second embodiment, the inclinometer 22 is mounted via its bushing 36 onto post 34 formed on the bottom of the valve casing (as viewed in FIG. 7) in the same manner as described with respect to the first embodiment of FIGS. 1–4. Thus, the inclinometer can be detached, and coupling 20′ can be used with or without the inclinometer.

The inclinometer tube 23 may be any clear plastic, such as PVC, cellulosic acetate, propionate or butyrate. Furthermore, the ball 24 may also be made of plastic so long as the relationship between the weight of the ball and its friction with the tube 23 permits the ball easily to roll or slide under the force of gravity to remain in the lowest portion of the tube. It has been assumed that the surface of the skin to be injected is always in the vertical plane, which condition can be easily obtained by tiltable operating tables and the like. If the patient's skin surface should be in any other plane, such as a horizontal one, it is clear that the orientation of the inclinometer can be adjusted so that the position of ball 24 will always be a correct indication of the angle of inclination.

I claim:

1. In an injection needle and syringe assembly having a syringe and an injection needle coupled to the syringe, the improvement comprising gravity-responsive inclinometer means mounted on the assembly for indicating the angle of inclination of the needle relative to a patient's skin.

2. The improvement as defined in claim 1 wherein said inclinometer means comprises arcuate track means and an indicating element freely riding on said track means for movement relative thereto in a vertical plane so that the position of said element relative to said track means indicates said angle of inclination.

3. The improvement as defined in claim 2 wherein said track means is an arcuate transparent tube having graduations for indicating said position of said element as a measure of said angle of inclination.

4. The improvement as defined in claim 3 wherein said indicating element is a ball.

5. The improvement as defined in claim 4 further comprising hollow coupling means interconnecting the needle and syringe, said coupling means having a first inlet coupled to the syringe and an outlet coupled to the needle, and mounting means for detachably and adjustably fixing said transparent tube to said coupling means.

6. The improvement as defined in claim 1 further comprising hollow coupling means interconnecting the needle and syringe, said coupling means having a first inlet coupled to the syringe and an outlet coupled to the needle, and mounting means for detachably and adjustably fixing said transparent tube to said coupling means.

7. The improvement as defined in claim 6 wherein said mounting means comprises: a post rigidly fixed to said coupling means, and a bushing fixed to said inclinometer means, said post and said bushing being dimensioned such that said post may be friction-fit within said bushing.

8. The improvement as defined in claim 5 further comprising a second inlet projecting from said coupling means and in fluid flow communication with the interior of said coupling means, and a three-way valve disposed at the junction of said coupling means and said second inlet for selectively forming a first flow path from said first inlet to said outlet and a second flow path from said second inlet to said outlet.

9. The improvement as defined in claim 8 further comprising means on said second inlet for coupling a syringe thereto.

* * * * *